United States Patent
Wils et al.

(10) Patent No.: US 6,730,781 B1
(45) Date of Patent: May 4, 2004

(54) PURIFICATION OF PLASMID DNA OF PHARMACEUTICAL QUALITY

(75) Inventors: Pierre Wils, Paris (FR); Monique Ollivier, Le Kremlin Bicetre (FR)

(73) Assignee: Gencell S.A. (FR)

( * ) Notice: Subject to any disclaimer, the term of this patent is extended or adjusted under 35 U.S.C. 154(b) by 603 days.

(21) Appl. No.: 09/153,838

(22) Filed: Sep. 15, 1998

Related U.S. Application Data

(63) Continuation of application No. PCT/FR97/00472, filed on Mar. 17, 1997.

(30) Foreign Application Priority Data

Mar. 21, 1996 (FR) ............................................. 96 03519

(51) Int. Cl.$^7$ .............................................. C07H 21/04
(52) U.S. Cl. ...................... 536/25.4; 536/23.5; 435/259
(58) Field of Search .............. 536/25.4, 23.5; 435/259

(56) References Cited

U.S. PATENT DOCUMENTS

| | | | | |
|---|---|---|---|---|
| 5,576,196 A | * | 11/1996 | Horn et al. ................. | 435/91.1 |
| 5,674,997 A | * | 10/1997 | Woodard et al. ........... | 536/25.4 |

FOREIGN PATENT DOCUMENTS

| | | |
|---|---|---|
| EP | 0313090 | 4/1989 |
| EP | 0325032 | 7/1989 |
| EP | 0375408 | 6/1990 |
| WO | WO 94/16075 | 7/1994 |
| WO | WO 95/21177 | 8/1995 |
| WO | WO 97/29113 | 8/1997 |

OTHER PUBLICATIONS

Johnson et al. Analytical Biochemistry, vol. 132, 1983, pp. 20–25.*

Cummings et al., Macro–Prep Ceramic Hydroxyapatite—New Life for an Old Chromatographic Technique, Separations for Biotech., vol. 3, Royal Society of Chemistry, 1994, pp. 134–140.

Ito et al., Sequence–specific DNA purification by triplex affinity capture, Proc. Natl. Acad. Sci, USA, vol. 89, pp. 495–498, Jan. 1992.

Jarrett, Affinity chromatography with nucleic acid polymers, J. of Chromatography, vol. 618 (1993), pp. 315–339.

Rajagopal et al., NMR Studies of Triple–Strand Formation from the Homopurine–Homopyrimidine Deoxyribonucleotides d(GA)4 and D(TC)4, Biochemistry, vol. 28, 1989, pp. 7859–7870.

Koji, Separation of proteins, nucleic acids and glycosides on hydroxyapatite.

* cited by examiner

*Primary Examiner*—James Ketter
(74) *Attorney, Agent, or Firm*—Finnegan, Henderson, Farabow, Garrett & Dunner, L.L.P.

(57) ABSTRACT

The invention is directed to a process for purifying double-stranded DNA, comprising using ceramic hydroxyapatite column chromatography. The invention is also directed to a purified recombinant plasmid DNA composition, comprising a chromosomal DNA content that is less than or equal to 0.01% as well as to a composition comprising DNA prepared by the foregoing process.

22 Claims, No Drawings

SEQUENCE LISTING

<160> NUMBER OF SEQ ID NOS: 15

<210> SEQ ID NO 1
<211> LENGTH: 25
<212> TYPE: DNA
<213> ORGANISM: Artificial Sequence

```
<220> FEATURE:
<223> OTHER INFORMATION: Description of Artificial Sequence: Poly-CTT
      containing oligonucleotide

<400> SEQUENCE: 1
gaggcttctt cttcttcttc ttctt                                              25

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Poly-CTT
      containing oligonucleotide

<400> SEQUENCE: 2
cttcttcttc ttcttcttct t                                                  21

<210> SEQ ID NO 3
<211> LENGTH: 56
<212> TYPE: DNA
<213> ORGANISM: Artificial Sequence
<220> FEATURE:
<223> OTHER INFORMATION: Description of Artificial Sequence:
      Oligonucleotide used to generate plasmid pXL 2675

<400> SEQUENCE: 3
agcttctcga gctgcaggat atcgaattcg gatcctctag agcggccgcg agctcc           56

<210> SEQ ID NO 4
<211> LENGTH: 56
<212> TYPE: DNA
<213> ORGANISM: Artificial Sequence
<220> FEATURE:
<223> OTHER INFORMATION: Description of Artificial Sequence:
      Oligonucleotide used to generate plasmid pXL 2675

<400> SEQUENCE: 4
agctggagct cgcggccgct ctagaggatc cgaattcgat atcctgcagc tcgaga           56

<210> SEQ ID NO 5
<211> LENGTH: 58
<212> TYPE: DNA
<213> ORGANISM: Artificial Sequence
<220> FEATURE:
<223> OTHER INFORMATION: Description of Artificial Sequence: sequence
      able to form a triple helix

<400> SEQUENCE: 5
gatccgaaga agaagaagaa gaagaagaag aagaagaaga agaagaagaa gaagaagg         58

<210> SEQ ID NO 6
<211> LENGTH: 58
<212> TYPE: DNA
<213> ORGANISM: Artificial Sequence
<220> FEATURE:
<223> OTHER INFORMATION: Description of Artificial Sequence: sequence
      able to form a triple helix

<400> SEQUENCE: 6
aattccttct tcttcttctt cttcttcttc ttcttcttct tcttcttctt cttcttcg         58

<210> SEQ ID NO 7
<211> LENGTH: 27
<212> TYPE: DNA
<213> ORGANISM: Escherichia coli
<220> FEATURE:
```

```
<400> SEQUENCE: 7
ccgaattctg gggaccaaag cagtttc                                27

<210> SEQ ID NO 8
<211> LENGTH: 27
<212> TYPE: DNA
<213> ORGANISM: Escherichia coli
<220> FEATURE:

<400> SEQUENCE: 8
ccaagcttca ctgttcacga cgggtgt                                27

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: triple
      helix forming oligonucleotide

<400> SEQUENCE: 9
aagggaggga ggagaggaa                                         19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: triple
      helix forming oligonucleotide

<400> SEQUENCE: 10
aaggagagga gggagggaa                                         19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: triple
      helix forming oligonucleotide

<400> SEQUENCE: 11
ttggtgtggt gggtgggtt                                         19

<210> SEQ ID NO 12
<211> LENGTH: 19
<212> TYPE: DNA
<213> ORGANISM: Escherichia coli
<220> FEATURE:

<400> SEQUENCE: 12
cttcccgaag ggagaaagg                                         19

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide complementary to Seq. I.D. No. 12

<400> SEQUENCE: 13
gaagggttct tccctctttc c                                      21
```

```
<210> SEQ ID NO 14
<211> LENGTH: 13
<212> TYPE: DNA
<213> ORGANISM: Escherichia coli
<220> FEATURE:

<400> SEQUENCE: 14
gaaaaaggaa gag                                                          13

<210> SEQ ID NO 15
<211> LENGTH: 17
<212> TYPE: DNA
<213> ORGANISM: Escherichia coli
<220> FEATURE:

<400> SEQUENCE: 15
aaaaaaggga ataggg                                                       17
```

PURIFICATION OF PLASMID DNA OF PHARMACEUTICAL QUALITY

This application is a continuation of international patent application No. PCT/FR97/00472, filed on Mar. 17, 1997, designating the United States.

The present invention relates to a novel process for purifying DNA. The process according to the invention enables pharmacologically utilizable double-stranded DNA to be purified rapidly. More specifically, the purification process according to the invention involves only diafiltration and chromatographic steps.

The techniques of gene and cell therapy are currently experiencing an extraordinary rate of growth. Nevertheless, these techniques involve the possibility of producing substantial quantities of DNA of pharmacological purity, in particular plasmid DNA. In fact, in these new therapies, the pharmaceutical often consists of DNA itself, and it is essential to be able to make this DNA in suitable quantities and to isolate and purify it in a manner which is appropriate for therapeutic use in man, in particular by way of the intravenous route.

These problems of quantity and purity have not been taken into account in the conventional methods for isolating DNA. As a result, it is not possible to adapt the methods which are employed in the laboratory for the purpose of purifying plasmid DNA within the pharmaceutical industry. Two of these laboratory methods are those which are most frequently employed and which give the best results. They consist of starting with a crude bacterial lysate and enriching it in plasmid DNA by removing the maximum possible quantity of contaminants. In particular, egg white lysozyme is used to break down the bacterial wall after which the lysate is centrifuged in order to remove the cell debris. The supernatant is then subjected to the action of a pancreatic RNase of animal origin, thereby removing the RNA, which at this time represents approximately 75% of the nucleic acids which are present.

The proteins are then precipitated with a phenol/chloroform/isoamyl alcohol mixture. The supernatant which is obtained following centrifugation is cleared of proteins and RNA but still contains large quantities of chromosomal DNA, which has to be removed during an additional step. This step consists of an ultracentrifugation in the presence of ethidium bromide and caesium chloride. The three types of nucleic acid, that is chromosomal DNA, plasmid DNA and RNA, vary in their ability to bind ethidium bromide. As a result, they separate into three distinct phases during ultracentrifugation on a caesium chloride gradient.

A variant of this protocol consists in following the action of the pancreatic RNase with a reduction in presence of an alkaline detergent, followed in turn by an extraction with phenol/chloroform. The DNA is then precipitated with ethanol, resuspended and reprecipitated with polyethylene glycol.

However, these two methods of obtaining a solution of plasmid DNA cannot be used for the industrial production of a product of pharmaceutical purity. Thus, the use of enzymes of animal origin poses a problem. Due to their origin, both the lysozyme and the pancreatic RNase entail the risk of introducing a viral contamination into the final product. Furthermore, the organic solvents are extremely toxic and have to be removed if it is desired to use the product as a pharmaceutical. These solvents also lead to a considerable increase in costs associated, in particular, with their storage, their use under conditions of maximum security and the removal of the toxic waste to which they give rise, and also because of the difficulty which is encountered in successfully verifying complete removal of such products from the final solution. As for the ethidium bromide, it is so toxic, mutagenic and teratogenic that its presence, even in traces, cannot be tolerated in a product that is meant for pharmaceutical purposes. The use of solvents, toxic reagents and also enzymes of animal origin is incompatible with an industrial process that conforms to good manufacturing practices.

The present invention describes a simple, and particularly efficient, novel process for purifying DNA. The process that is described in the present application enables a DNA of very high purity to be produced in large quantities. Particularly advantageously, the process that is described in the present application makes it possible to avoid using toxic organic solvents and enzymes of animal origin. It also makes it possible to dispense with large numbers of tedious centrifugations which are difficult to extrapolate and are of low yield because, in particular, of precipitation steps using PEG, ammonium acetate or $CaCl_2$. The process according to the invention also enables large quantities of DNA (100 mg, 1 g, 10 g or more) to be obtained in a single batch, without any particular technical difficulty. Furthermore, the process according to the invention involves methods which are compatible with good manufacturing practices and makes it possible to obtain a DNA of pharmaceutical quality.

The invention relates, first of all, to a process for purifying double-stranded DNA, which process enables large quantities of plasmid DNA of pharmaceutical purity to be obtained very rapidly and involves a chromatographic step on a column of hydroxyapatite which is in ceramic form. While hydroxyapatite in crystalline form was already disclosed, the use of this hydroxyapatite was difficult and limited owing to its fragility. The ceramic form is much more resistant both physically and chemically.

Preferably, the process of the invention comprises two chromatographic steps, with at least one of them being a chromatographic step on hydroxyapatite.

Advantageously, the second chromatographic step is a step of affinity chromatography or ion exchange chromatography. The order in which the two chromatographic steps are carried out is immaterial.

According to one particularly preferred embodiment, the process according to the invention comprises a chromatographic step on a column of hydroxyapatite and a step of triple-helix affinity chromatography. Triple-helix affinity chromatography is based on using a support to which is covalently coupled an oligonucleotide which is able to form, by means of hybridization, a triple helix with a specific sequence which is present in the said DNA. The order in which the two chromatographic steps are carried out is immaterial.

According to another embodiment, the process of the invention comprises one step of chromatography on a column of hydroxyapatite and one step of ion exchange chromatography.

Advantageously, the process of the invention additionally comprises a diafiltration step. The latter is generally carried out prior to the chromatographic steps.

An important step in the process of the invention involves chromatography on a column of hydroxyapatite.

Hydroxyapatite is a complex calcium phosphate which includes ten calcium atoms. The ceramic form, which is more stable than the crystalline form, was developed by Bio-Rad Laboratories and Asahi Optical Co., Ltd. The ceramic compound has the same properties as the crystalline compound without having the physical limitations of the latter; while this material is particularly used in chromatography for purifying proteins, it offers advantages, and enables very good results to be obtained, in the purification of nucleic acids. It is macroporous, spherical and chemically and physically very stable and can be reused many times over without losing efficacy. This ceramic form can withstand high pressures, very high pH values, very rapid flows and organic solvents.

Chromatography on a column of ceramic hydroxyapatite is a special type of chromatography which is strictly neither affinity chromatography nor ion exchange chromatography. It imprints its properties to these two types of chromatography and it could be defined as to pseudo affinity chromatography and pseudo ion exchange chromatography.

The nucleic acids bind to the hydroxyapatite by virtue of interactions between the phosphate groups of the skeleton of the polynucleotide and the calcium residues of the support. The nucleic acids can be eluted differentially by varying the ionic strength of the phosphate buffers. The nucleic acids can thus be separated from the proteins and, among themselves, the DNA can be separated from the RNA and the single-stranded DNA can be separated from the double-stranded DNA. The RNA is the nucleic acid which binds least firmly and can be eluted with a buffer of relatively low ionic strength. The single-stranded DNA is also less strongly bound than is the double-stranded DNA, which is more firmly bound to the support and requires a stronger buffer.

The biological material, in a phosphate buffer of low ionic strength, is loaded on a column. The DNA and RNA nucleic acids are bound. A second buffer, of higher ionic strength, is then used to elute the RNA, which is almost completely removed at this stage. A third buffer of greater ionic strength is used to elute the double-stranded DNA, which is collected. The use of hydroxyapatite in the process of the invention makes it possible to recover double-stranded DNA which has a very high degree of purity.

As indicated above, a preferred embodiment of the invention additionally comprises a step of triple-helix affinity chromatography.

Triple-helix affinity chromatography consists in passing the solution which has been obtained over a support to which is covalently coupled an oligonucleotide which is able to form, by means of hybridization, a triple helix with a specific sequence which is present in the DNA to be purified (WO96/18744).

The specific sequence can be a sequence which is naturally present in the double-stranded DNA or a synthetic sequence which is artificially introduced into this double-stranded DNA. The oligonucleotides which are used in the present invention are oligonucleotides which hybridize directly with the double-stranded DNA. These oligonucleotides can contain the following bases:

thymidine (T), which is able to form triplets with the AT doublets of the double-stranded DNA (Rajagopal et al., Biochem 28 (1989) 7859);

adenine (A), which is able to form triplets with the AT doublets of the double-stranded DNA;

guanine (G), which is able to form triplets with the GC doublets of the double-stranded DNA;

protonated cytosine (C+), which is able to form triplets with the GC doublets of the double-stranded DNA (Rajagopal et al., loc. cit.);

uracil (U), which is able to form triplets with the base pairs AU or AT.

Preferably, the oligonucleotide which is used comprises a cytosine-rich homopyrimidine sequence and the specific sequence which is present in the DNA is a homopurine/homopyrimidine sequence. The presence of cytosines makes it possible to have a triple helix which is stable at acid pH, when the cytosines are protonated, and destabilized at alkaline pH, when the cytosines are neutralized.

For a triple helix to be formed by hybridization, it is important that the oligonucleotide and the specific sequence which is present in the DNA are complementary. In this regard, an oligonucleotide and a specific sequence which are perfectly complementary to each other are used in the process of the invention in order to obtain the best yields and the greatest degree of selectivity. The oligonucleotide can in particular be a poly-CTT oligonucleotide and the specific sequence can be a poly-GAA specific sequence. The oligonucleotide having the sequence 5'-GAGGCTTCTT CTTCTTCTTCTCTT-3' (GAGG(CTT)$_7$); (SEQ ID NO:1), in which the bases GAGG do not form a triple helix t enable the oligonucleotide to be spaced from the coupling arm, may be mentioned by way of example. The sequence (CTT)$_7$ (SEQ ID NO:2) may also be mentioned. These oligonucleotides are able to form a triple helix with a specific sequence which comprises complementary motifs (GAA). The specific sequence can, in particular, be a region which comprises 7, 14 or 17 GAA motifs, as described in the examples.

Another sequence of specific interest is the sequence:

5'-AAGGGAGGGAGGAGAGGAA-3' (SEQ ID NO:9).

This sequence forms a triple helix with the oligonucleotides

5'-AAGGAGAGGAGGGAGGGAA-3' (SEQ ID NO:10) or

5=-TTGGTGTGGTGGGTGGGTT-3' (SEQ ID NO:11).

In this case, the oligonucleotide binds in an antiparallel orientation to the polypurine strand. These triple helices are only stable in the presence of $Mg^{2+}$ (Vasquez et al., Biochemistry, 1995, 34, 7243–7251; Beal and Dervan, Science, 1991, 251, 1360–1363).

As indicated above, the specific sequence can be a sequence which is naturally present in the double-stranded DNA or a synthetic sequence which is artificially introduced into this double-stranded DNA. It is particularly advantageous to use an oligonucleotide which is able to form a triple helix with a sequence which is naturally present in the double-stranded DNA, for example in the origin of replication of a plasmid or in a marker gene. In this regard, applicants have carried out sequence analyses on plasmids and have been able to demonstrate that certain regions of these DNAs, in particular in the origin of replication, possess homopurine/homopyrimidine regions. The synthesis of oligonucleotides which are able to form triple helices with these natural homopurine/homopyrimidine regions advantageously enables the process of the invention to be applied to unmodified plasmids, in particular commercial plasmids of the pUC, pBR322, pSV, etc. type. Of the homopurine/homopyrimidine sequences which are naturally present in a double-stranded DNA, mention may be made of a sequence which comprises all or part of the sequence 5'-CTTCCCGAAGGGAGAAAGG-3' (SEQ ID NO:12), which is present in the *E. coli* ColE1 origin of replication. In this case, the oligonucleotide forming the triple helix possesses the sequence: 5' GAAGGGTTCTTCCCTCTTTCC-3' (SEQ ID NO:13) and binds alternately to the two strands of the double helix, as described by Beal and Dervan (J. Am. Chem. Soc. 1992, 114, 4976–4982) and Jayasena and Johnston (Nucleic Acids Res. 1992, 20, 5279–5288). The sequence 5'-GAAAAAGGAAGAG-3' (SEQ ID NO:14) of the gene for the b-lactamase of plasmid pBR322 (Duval- Valentin et al., Proc. Natl. Acad. Sci. USA, 1992, 89, 504–508) may also be mentioned. The use of an oligonucleotide which is able to form a triple helix with a sequence which is present in an origin of replication or a marker gene is particularly advantageous since it enables all the DNA containing the said origin of replication or the said marker gene to be purified using the same oligonucleotide. It is not necessary, therefore, to modify the plasmid or the double-stranded DNA in order to incorporate an artificial specific sequence into it.

Although sequences which are perfectly complementary are preferred, it is nevertheless to be understood that certain mispairings between the sequence of the oligonucleotide and the sequence which is present in the DNA can be tolerated as long as they do not lead to too great a loss of affinity. The sequence 5'-AAAAAAGGGAATAAGGG-3' (SEQ ID NO:15), which is present in the gene for E. coli b-lactamase, may be mentioned. In this case, the thymine which interrupts the polypurine sequence can be recognized by a guanine of the third strand, thereby forming an ATG triplet which is stable when it is flanked by two TAT triplets (Kiessling et al., Biochemistry, 1992, 31, 2829–2834).

According to one particular embodiment, the oligonucleotides of the invention comprise the sequence (CCT)n, the sequence (CT)n or the sequence (CTT)n, in which n is an integer between 1 and 15 inclusive. It is particularly advantageous to use sequences of the (CT)n or (CTT)n type. Thus, the applicant found that the purification yield was influenced by the quantity of C's in the oligonucleotide. In particular, as shown in Example 7, the purification yield increases when the oligonucleotide includes fewer cytosines. It is to be understood that the oligonucleotides of the invention can also combine (CCT), (CT) or (CTT) motifs.

The oligonucleotide which is used can be natural (composed of unmodified, natural bases) or chemically modified. In particular, the oligonucleotide can advantageously exhibit certain chemical modifications which increase its resistance to, or its protection from, nucleases, or increase its affinity for the specific sequence.

According to the present invention, oligonucleotide is also understood to mean any sequence of nucleosides whose skeleton has been modified with the aim of making it more resistant to nucleases. Possible modifications which may be mentioned are phosphorothioate oligonucleotides which are able to form triple helices with DNA (Xodo et al., Nucleic Acid Res., 1994, 22, 3322–3330) and also oligonucleotides which possess formacetal or methylphosphonate skeletons (Matteucci et al., J. Am. Chem. Soc., 1991, 113, 7767–7768). Oligonucleotides which have been synthesized with nucleotide a-anomers and which also form triple helices with DNA may also be employed (Le Doan et al., Nucleic Acids Res., 1987, 15, 7749–7760). Another modification of the skeleton is the phosphoramidate bond. Mention may be made, by way of example, of the phosphoramidate N3'-P5' internucleotide bond which was described by Gryaznov and Chen and which yields oligonucleotides which form particularly stable triple helices with DNA (J. Am. Chem. Soc., 1994, 116, 3143–3144). Other modifications of the skeleton which may be mentioned are the use of ribonucleotides, of 2'-O-methylribose, of phosphodiester, etc. (Sun and Hélène, Curr. Opinion Struct. Biol., 116, 3143–3144). Finally, the phosphorus-containing skeleton can be replaced by a polyamide skeleton as in the PNA's (peptide nucleic acids), which can also form triple helices (Nielsen et al., Science, 1991, 254, 1497–1500; Kim et al., J. Am. Chem. Soc., 1993, 115, 6477–6481) or by a guanidine-based skeleton, as in the DNG's (deoxyribonucleic guanidine, Proc. Natl. Acad. Sci. USA, 1995, 92, 6097–6101), which are polycationic analogues of DNA and which also form triple helices.

The thymine of the third strand can also be replaced with a 5-bromouracil, thereby increasing the affinity of the oligonucleotide for DNA (Povsic and Dervan, J. Am. Chem. Soc., 1989, 111, 3059–3061).

The third strand can also contain unnatural bases, among which may be mentioned 7-deaza-2'-deoxyxanthosine (Milligan et al., Nucleic Acids Res., 1993, 21, 327–333), 1-(2-deoxy-b-D-ribo-furanosyl)-3-methyl-5-amino-1H-pyrazolo[4,3-d]-pyrimidin-7-one (Koh and Dervan, J. Am. Chem. Soc., 1992, 114, 1470–1478), 8-oxoadenine, 2-aminopurine, 2'-O-methylpseudoisocytidine, or any other modification known to the skilled person (see Sun and Hélène, Curr. Opinion Struct. Biol., 1993, 3, 345–356, for a review).

The purpose of another type of modification of the oligonucleotide is more specifically that of improving the interaction and/or the affinity between the oligonucleotide and the specific sequence. In particular, a very advantageous modification according to the invention consists in methylating the cytosines of the oligonucleotide. The oligonucleotide which has thus been methylated exhibits the noteworthy property of forming a stable triple helix with the specific sequence in pH ranges which are closer to neutrality ($\geqq 5$). It therefore makes it possible to work at pH values which are higher than is the case for oligonucleotides of the prior art, that is at pH values at which there is much less risk of degrading the plasmid DNA.

The length of the oligonucleotide which is employed in the process of the invention is at least 3 bases and preferably between 5 and 30 bases. Advantageously, an oligonucleotide is used whose length is greater than 10 bases. The length may be modified by the skilled person from case to case in accordance with the sought-after selectivity and stability of the interaction.

The oligonucleotides according to the invention may be synthesized by any known technique. In particular, they can be prepared using nucleic acid synthesizers. Any other method known to the skilled person may of course also be employed.

In general, the oligonucleotide is functionalized in order to enable it to be coupled covalently to the support. Thus, it can be modified by a terminal thiol, amine or carboxyl group in the 5' or 3' position. In particular, the addition of a thiol, amine or carboxyl group makes it possible, for example, to couple the oligonucleotide to a support which is carrying disulphide, maleimide, amine, carboxyl, ester, epoxide, cyanogen bromide or aldehyde functions. These couplings are formed by establishing disulphide, thioether, ester, amide or amine bonds between the oligonucleotide and the support. Any other method known to the skilled person, such as bifunctional coupling reagents, for example, may also be employed.

Furthermore, in order to improve the hybridization with the coupled oligonucleotide, it can be advantageous for the oligonucleotide to contain an "arm" and a sequence of "spacer" bases. Thus, the use of an arm makes it possible to bind the oligonucleotide at a chosen distance from the support, thereby improving its conditions for interacting with DNA. The arm advantageously consists of a linear carbon chain comprising from 1 to 18, preferably 6 or 12, ($CH_2$) groups and of an amine which permits binding to the column. The arm is connected to a phosphate of the oligonucleotide or of a "spacer" which is composed of bases which do not interfere with the hybridization. Thus, "the spacer" can consist of purine bases. As an example, "the spacer" can consist of the sequence GAGG. The arm is advantageously made up of a linear carbon chain comprising 6 or 12 carbon atoms.

Various types of support may be used for implementing the present invention. These supports can be bulk or column-preconditioned functionalized chromatographic supports, functionalized plastic surfaces or magnetic or non-magnetic functionalized latex beads. They are preferably chromatographic supports. By way of example, the chromatographic supports which can be used are agarose, acrylamide or dextran and their derivatives (such as Sephadex, Sepharose, Superose, etc.), polymers such as poly (styrenedivinylbenzene) or grafted or non-grafted silica, for example. The chromatography columns can function in diffusion mode or perfusion mode.

In order to obtain better purification yields, it is particularly advantageous to use, in the plasmid, a sequence which includes several positions for hybridizing with the oligonucleotide. Thus, the presence of several hybridization positions favours interactions between the said sequence and the oligonucleotide, thereby leading to an improvement in purification yields. Thus, for an oligonucleotide which includes n (CCT), (CT) or (CTT) motif repetitions, it is preferable to use a DNA sequence which includes at least n complementary motifs, preferably n+1 complementary motifs. Thus, a sequence which carries n+1 complementary motifs offers two hybridization positions to the oligonucleotide. Advantageously, the DNA sequence includes up to 11 hybridization positions, that is n+10 complementary motifs.

According to another embodiment, the chromatography on a ceramic hydroxyapatite column is followed or preceded by a step of chromatography on an anion exchange column. Preference is given to using an exchange column of weak anions. Thus, strong anions have the property of binding the DNA very strongly, in fact so strongly that it is very difficult to recover the product (the yield is then less than 60%). For this reason, weak anion exchange materials that do not retain plasmid DNA but which bind residual RNA are used.

As indicated above, the process according to the invention advantageously includes a diafiltration step. Diafiltration is a step for concentrating the sample, during which water and small molecules (such as salts, proteins and nucleic acids of small size) which are present in the clear lysate are removed. The salts are replaced with a phosphate buffer for the chromatography. After diafiltration, the solution is from 5 to 50 times more concentrated than the starting solution (the concentration factor depends on the volume of the starting solution).

The use of diafiltration provides several advantages. It makes it possible, inter alia, to avoid employing organic solvents, such as isopropanol, whose use would necessitate an explosion-proof installation. Furthermore, this technique can be used for a very wide range of volumes. Thus, it is only necessary to increase the area of the membranes in accordance with the volume to be treated.

Advantageously, use is made, for the diafiltration, of an apparatus which serves as the support for a modified polyether sulphone or modified cellulose acetate membrane which permits liquid flow at a rate which can be regulated. These membranes are defined by their cut-off point, which is the nominal maximum size of the molecules which are able to cross the said membrane. Related to a true value, a membrane whose cut-off point is 100 kD enables molecules of a size greater than 30 kD to be retained.

A preferred process according to the invention comprises the following steps:

diafiltration, chromatography on a column of ceramic hydroxyapatite, and affinity chromatography by means of specific hybridization between a DNA sequence and an oligonucleotide, with the formation of a triple helix.

The process according to the present invention can be used to purify any type of double-stranded DNA. This double-stranded DNA can, for example, be circular DNA, such as a plasmid which is generally carrying one or more genes of therapeutic interest. This plasmid can also carry an origin of replication, a marker gene, etc. This process also enables the linear or circular DNA carrying a sequence of interest to be purified from a mixture which comprises DNA's of different sequences.

In general, the starting DNA is produced by a host microorganism which has been modified by recombinant DNA techniques. In this regard, the host which harbours the double-stranded DNA to be recovered is first of all replicated and amplified. Standard fermentation techniques enabling a high cell density to be obtained are used for this purpose. The most commonly employed technique is that termed the "fed-batch" technique, which is amply described in the literature (Jung et al., *Ann. Inst. Pasteur/Microbiol.* 1988, 139, p.129–146; Bauer et al., *Biotechnol. Bioeng.* 1976, 18, p.81–94).

The fermentation is followed by a lysis of the cells. Either a mechanical system or a chemical system can be used to lyse the cells, depending on the type of cells concerned or depending on whether it is desired to work on a crude lysate or a clear lysate. Systems which do not denature the DNA (shaking, thermal shock or osmotic shock) are preferably used for the mechanical lysis. These methods are not suitable for extracting DNA from prokaryotic cells. Thus, the mechanical treatments which are used for breaking prokaryotic cells have the effect of denaturing the DNA. Mechanical lysis is preferably reserved for eukaryotic cells, with preference being given to chemical lysis for prokaryotic cells.

Prokaryotic cells are chemically lysed using any technique known to the skilled person (detergents or lysozymes, where appropriate combined with a thermal shock, etc.). A mixture of sodium hydroxide solution and SDS is preferably employed. During this treatment, the pH rises to 12. The pH of the lysate which has thus been obtained is then brought back to approximately pH 6, which leads to precipitation of the proteins of a part of the chromosomal DNA and the RNA. This precipitate is removed by centrifugation.

A preferred embodiment of the invention consists in first of all subjecting the cells harbouring the double-stranded DNA to be purified to a chemical lysis in order to obtain a clear lysate. The resulting clear lysate is subjected to a diafiltration, and it is the concentrate which is thus obtained which is chromatographed on a column of ceramic hydroxyapatite.

The cell lysate can be a lysate of prokaryotic or eukaryotic cells.

Examples of prokaryotic cells which may be mentioned are the bacteria *E. coli, B. subtilis, S. typhimurium*, or *Streptomyces*. Eukaryotic cells which may be mentioned are animal cells, yeasts, fungi, etc., and, more specifically, the yeasts Kluyveromyces or Saccharomyces or COS cells, CHO cells, C127 cells, NIH3T3 cells, etc.

The process of the invention is particularly advantageous since it enables plasmid DNA of very high purity to be obtained rapidly and simply. In particular, as illustrated in the examples, this process enables the plasmid DNA under consideration to be separated efficiently from contaminating components such as fragmented chromosomal DNA, RNA, endotoxins, proteins, nucleases, etc. More specifically, the process of the invention enables double-stranded DNA preparations, in particular plasmid DNA preparations, to be obtained which are virtually free of chromosomal DNA (<0.5%). Furthermore, the content of endotoxins in the DNA preparations which are obtained is very low (<50 EU/mg), a value which is compatible with pharmaceutical use.

The applicant has demonstrated, very surprisingly, that the combination of the two above-described steps, namely chromatography on a column of hydroxyapatite followed or preceded by a triple helix chromatography, enables plasmid DNA preparations to be obtained which have a chromosomal DNA content of 0.01%. Very preferably, the invention also relates to plasmid DNA preparations which have a chromosomal DNA content which is less than or equal 0.01%.

The invention also relates to preparations of plasmid DNA which have an endotoxin content which is less than 50 EU/mg, preferably less than 10 EU/mg. The endotoxin content is therefore well below the authorized content, which is 350 EU/injection for a person weighing 70 kg (one EU is one endotoxin unit and is equal to 100 pg).

The present invention therefore describes compositions which comprise plasmid DNA which can be used pharmaceutically, in particular in in-vivo or ex-vivo gene or cell therapy. In this regard, the invention also relates to a pharmaceutical composition which comprises linear or plasmid double-stranded DNA which has been prepared in accordance with the above-described process.

The compositions can comprise plasmid DNA which is "naked" or combined with transport vectors such as liposomes, nanoparticles, cationic lipids, polymers, proteins or recombinant viruses, etc.

The present application will be described in more detail with the aid of the following examples, which should be regarded as being illustrative and not limiting.

MATERIAL AND METHODS

1. Construction of the Plasmid pXL2784

A specific plasmid, pXL2784, has been used in the experiments which follow. This plasmid includes a cassette containing the cytomegalovirus promoter, the gene encoding luciferase and a homopurine/homopyrimidine sequence, $(GAA)_{17}$. The construction of this plasmid is described below. It will naturally be understood that the process of the invention is not limited to the plasmid described.

1.1. Description of Plasmid pXL2784

Plasmid pXL2784 is constructed from the plasmid vector pXL2675 (2.513 kb), which is a minimal replicon of plasmid ColE1 and is derived from the pBluescript plasmid (ORI) and has, as selection marker, the transposon Tn5 gene encoding resistance to kanamycin. Plasmid pXL2784 also contains a homopurine/homopyrimidine sequence, $(GAA)_{17}$, which is derived from the plasmid pXL2563 and which can bind to a $(CTT)_n$ oligomer, in which n=1 to 17, in order to generate a triple helix structure locally and to enable purification to take place by means of affinity chromatography. Plasmid pXL2784 possesses the cer locus (382 bp) which is derived from plasmid ColE1 and which is cloned into the plasmid pXL565; the cer locus contains a site-specific sequence for the XerC/XerD recombinases and leads to resolution of plasmid multimers. The transgene which is cloned into this plasmid pXL2784 is an expression cassette (3.3 kb) consisting of the luc gene encoding *Photinus pyralis* luciferase under the control of the human cytomegalovirus CMV P promoter, with this cassette coming from the plasmid pXL2622.

The size of the plasmid is 6390 bp. The map of plasmid pXL2784 is depicted in FIG. 1 and its construction is detailed below.

1.2. Minimal Vector pXL2675

After having rendered the BsaI end blunt using the Klenow fragment, the 1.15 kb BsaI/PvuII fragment from plasmid pBKS+ (Stratagene) was cloned together with the 1.2 kb SmaI fragment from plasmid pUC4KIXX (Pharmacia) in order to generate plasmid pXL2647.

The oligonucleotide 5543:

5'-AGCTTCTCGA GCTGCAGGAT ATCGAATTCG GATCCTCTAG AGCGGCCGCG AGCTCC-3' (SEQ ID NO:3)

and the oligonucleotide 5543:

5'-AGCTGGAGCT CGCGGCCGCT CTAGAGGATC CGAATTCGAT ATCCTGCAGC TCGAGA-3' (SEQ ID NO:4)

were hybridized together and then cloned into the HindIII side of pXL2647 in order to generate plasmid pXL2675. This plasmid contains the HindIII, XhoI, PstI, EcoRV, EcoRI, BamHI, XbaI, NotI, SstI multicloning site between the origin of replication and the gene encoding resistance to kanamycin.

1.3. Luciferase Cassette in Plasmid pXL2622

The CMV promoter which is contained in the 660 bp MluI/HindIII fragment from plasmid pcDNA3 (supplied by Invitrogen) was cloned between the MluI and HindIII sites of basic plasmid pGL2 (from Promega, contains the gene for luciferase) in order to generate plasmid pXL2622.

1.4. Plasmids pXL2563 and pMTL22-TH Containing a Sequence Which is Able to Form a Triple Helix With an Oligonucleotide.

The oligonucleotide 4817:

5'-GATCCGAAGA AGAAGAAGAA GAAGAAGAAG AAGAAGAAGA AGAAGAAGAA GAAGAAGG-3' (SEQ ID NO:5)

and the oligonucleotide 4818:

5'-AATTCCTTCT TCTTCTTCTT CTTCTTCTTC TTCTTCTTCT TCTTCTTCTT CTTCTTCG-3' (SEQ ID NO:6)

were hybridized together and cloned into the EcoRI and BamHI sites of plasmid pBluescriptII KS in order to form plasmid pXL2563. The 62 bp EcoRI/BamHI fragment is cloned into the EcoRI and BamHI sites of plasmid pMTL22 (P. Minton 1988 Gene 68:139) in order to generate plasmid pMTL22-TH.

1.5. Plasmids pXL565 and pXL2781 Containing the cer Locus

The 382 bp HpaII fragment from plasmid ColE1 (P-L Biochemicals) was cloned into the AccI site of plasmid M13 mp7 (Messing et al., 1981 Nucleic Acids Res 9:309) in order to form plasmid pXL565. The 382 bp BamHI fragment from pXL565 was then cloned into the BglII site of plasmid pSL301 (Invitrogen) in order to give rise to plasmid pXL2781.

1.6 Construction of Plasmid pXL2784

The 382 bp BamHI/XhoI fragment from plasmid pXL2781, containing the cer locus, is cloned into the BamHI and XhoI sites of plasmid pXL2675 in order to give rise to plasmid pXL2782.

The 62 bp BglII/BamHI fragment from plasmid pMTL22-TH, containing the $(GAA)_{17}$ sequence, is cloned into the BamHI site of plasmid pXL2782 in order to form plasmid pXL2783.

Finally, the 3.3 kb SalI/SpeI fragment from plasmid pXL2622, containing the luciferase cassette, is cloned into the XhoI and NheI sites of plasmid pXL2783 in order to give rise to plasmid pXL2784. It will of course be understood that any other cassette for expressing a gene can be inserted in place of the luciferase cassette.

The strain DH1 (Mariatis et al., 1989) containing this plasmid is cultured in fermenters of 2, 7 and up to 800 liters. Other strains can also be employed.

2. Fermentation

The plasmid DNA-harbouring host which is to be cultured can be obtained by standard fermentation techniques (Jung et al., *Ann. Inst. Pasteur/Microbiol.* 1988, 139, p.129–146; Bauer et al., *Biotechnol. Bioeng.* 1976, 18, p.81–94), with the fed-batch technique being preferred. Following fermentation, the cells are recovered either by means of conventional centrifugation (10000 rpm for 20 min), in the case of a laboratory-scale preparation, that is for volumes less than 5 l, or by means of continuous centrifugation in the case of more substantial volumes left. (industrial volumes which can amount to several hundreds of liters). The cells which have thus been recovered can be used immediately or else be frozen at −80° C.

3. Chemical Lysis (Clear Lysate)

The cells are thawed, where appropriate, and then lysed. Chemical lysis can be broken down into three steps. The first consists in resuspending the cells in a 25 mM Tris, pH 6.8, 50 mM glucose, 10 mM ETDA buffer or equivalent. The cells are then lysed in a mixture containing 0.2 M NaOH and 1% SDS. The pH of the solution is approximately 12. The choice of an ionic detergent is essential since a non-ionic detergent gives extraction yields which are 10 times lower. The lysis is followed by a pseudo-neutralization of the medium in the presence of potassium acetate (the final pH of the solution is between 5.5 and 6). This acidification of the medium results in the appearance of a precipitate containing the proteins and part of the chromosomal DNA and the RNA. This precipitation is due to reaction of the sodium dodecyl sulphate (SDS) with the potassium acetate, which together form a white precipitate of potassium dodecyl sulphate.

The precipitate has to be removed. To do this, the mixture is either centrifuged in buckets (8000 rpm for 15 min), if the volumes are less than 5 liters, or centrifuged continuously if the volumes are greater (>5 liters). Another method of removing the supernatant consists in filtering through a depth filter which is of a porosity greater than or equal to 20 mm (PALL, profile II, used in accordance with the manufacturer's specifications).

4. Diafiltration

The supernatant which is recovered after the chemical lysis is subjected to a diafiltration in order to concentrate the plasmid DNA and remove the molecules of small molecular weight, in particular the salts which are present at high concentrations. This diafiltration is effected through a membrane which has a cut-off point of between 50 and 300 kD, depending on the size of the plasmids. A membrane with a cut-off point of 100 kD is preferably used. The value of 100 kD is a nominal value which is given by proteins which are spherical molecules. In the case of nucleic acid molecules, which have a different spatial structure, it is considered that all molecules having a molecular weight less than 30 kd are removed. The quantity of DNA present in the solution after diafiltration and the quantity present in the clear lysate are measured by HPLC. The ratio determined in this way gives the yield for this step, which is greater than or equal to 80%.

The salts are removed during this diafiltration. They are replaced by 10 mM phosphate buffer. It is consequently possible to apply the product directly to a chromatography column, in particular a Ceramic Hydroxyapatite™ chromatography column.

The plasmid DNA which results from the triple helix affinity chromatography is diafiltered once again in order to concentrate the sample and remove undesirable salts. This enables the product to be equilibrated in the appropriate formulation buffer. For this, a diafiltration is carried out through a membrane which has a cut-off point of between 10 and 50 kD. The yield is greater than 80%.

The product is subsequently sterilized by filtration and subjected to analyses prior to formulation.

5. Chromatography on a Column of Ceramic Hydroxyapatite™

The Ceramic Hydroxyapatite™ gel is poured into a column which is of a size which is appropriate for the volume of the sample to be purified and in accordance with the purity of the starting sample. In order to determine the size of the column and the volume of the gel, the quantity of DNA which is present, in mg/ml, in the starting solution is measured by HPLC. It is reckoned that at least 0.1 mg of DNA is bound per ml of Hydroxyapatite, it being possible for this value to vary up to 1 mg, if not more, depending on the quantity of RNA which is present in the starting solution. The RNA binds to the gel and the greater the RNA quantity is the less DNA will be able to bind. The RNA is removed by differential elution. The column is equilibrated in a phosphate buffer of low ionic strength (10 MM). The sample is loaded onto the gel at a linear flow rate of 50 cm/h. The gel is then washed with a phosphate buffer of higher conductivity (150 mM). The major part of the RNA contained in the sample is removed at this stage. The plasmid DNA is eluted by once again increasing the conductivity of the phosphate buffer (250 mM). The final contaminants are removed by applying 0.5 N NaOH, which is neutralized with high molarity (500 mM) phosphate buffer before any reuse of the column. When pharmaceutical production is involved, this support has the advantage of being able to withstand an in-situ chemical decontamination since it is resistant both to 0.5 M sodium hydroxide solution, which is a standard cleaning agent in chromatography, and to high concentrations of ethanol.

The resolution of the ceramic hydroxyapatite is excellent. This step of the process removes more than 80% of the RNA and 99.9% of the chromosomal DNA and decreases the content of endotoxins by a factor of 1000. Furthermore, this technique avoids using any enzymes of bovine or other origin (no RNase, and no proteinase K); in addition, the resistance of the ceramic hydroxyapatite to chemical agents has to date enabled us to use it more than 40 times without any problem of reproducibility. The chromatographic yield is greater than or equal to 80%.

6. Affinity Chromatography With Formation of a Triple Helix 6.1. Preparation of the Column Material: The column which is used is an NHS (N-hydroxysuccinimide, Pharmacia)-activated HiTrap column of 5 ml which is connected to a peristaltic pump (flow rate<1 ml/min). The specific oligonucleotide which is used possesses a 5' $NH_2$ group.

The following buffers are used in this example:

Coupling buffer: 0.2 M $NaHCO_3$, 0.5 M NaCl, pH 8.3.

Buffer A: 0.5 Methanolamine, 0.5 M NaCl, pH 8.3.

Buffer B: 0.1 M acetate, 0.5 M NaCl, pH 4.

Method: The column is washed with 30 ml of 1 mM HCl, and the oligonucleotide, diluted in the coupling buffer (250 nmol in 5 ml), is then loaded onto the column, which is left at ambient temperature for 30 minutes. The column is washed 3 times, in succession, with 30 ml of buffer A and then with 30 ml of buffer B. The oligonucleotide is in this way bound covalently to the column by means of a CONH bond. The column is stored at 4° C. and can be used at least four times.

6.2. Plasmid Purification

Material:

Plasmid pXL 2784 (described in 1) was purified on the HiTrap column, which was coupled to the oligonucleotide described in 7.1. The following buffers were used during this purification:

Buffer F: 2 M NaCl, 0.2 M acetate, pH 4.5.

Buffer E: 1 M Tris-HCl, pH 9, 0.5 mM EDTA.

Method:

The column is washed with buffer F and the solution containing the plasmid is then loaded onto the column and incubated at ambient temperature for at least two hours. The column is washed with buffer F, after which elution is carried out using buffer E.

7. Ion Exchange Chromatography

The prepurified sample is then subjected to chromatography on a weak anion exchange column. Thus, strong anions have the property of binding the DNA very strongly, in fact so strongly that it is very difficult to recover the product (the yield is then less than 60%). For this reason, the applicant uses weak anion exchange materials which do not retain the plasmid DNA but which bind the residual RNA. Preference is therefore given to using a weak anion exchange material of the DEAE Sepharose or DEAE hyper D type, or equivalent. The gel is equilibrated in 10 mM phosphate buffer and the sample, which derives from the step of chromatography on Ceramic Hydroxyapatite, is loaded directly onto the gel. The RNA which is bound is then removed by applying a concentrated solution of NaCl. The chemical decontamination can be effected using a 0.5M solution of sodium hydroxide, thereby making it possible to work under good hygiene conditions (removal of endotoxins and elimination of the risk of microbial contamination).

8. The Use of HPLC to Assay the Plasmid DNA in Complex Samples

The object of this method is to be able to quantify the plasmid DNA during the various purification steps in order to determine yields. This makes it possible to assess the efficiency of the different operations both quantitatively and qualitatively.

The following technique is used:

The chromatographic support is a Poros R2 gel from Perseptive Biosystems. This is a polystyrene-divinylbenzene support whose particle size is 10 μm. The size of the perfusion pores is from 6000 to 8000 ångströms, with the size of the diffusion pores being from 500 to 1000. The volume of the gel is 1.7 ml.

Ion pair chromatography is employed. The solvent system is water, triethylamine acetate, pH 7.1/triethylamine acetate 90% acetonitrile.

The flow rate is 3 ml/min. We have defined the gradient so as to distinguish the plasmid DNA from the RNA.

The reference sample is a plasmid DNA which was purified on Qiagen in accordance with the manufacturer's instructions. On agarose gel, this sample only contains ocDNA and cccDNA. It only gives a single peak in HPLC. Its concentration was determined by measuring its OD at 260 nm and taking as a basis that 1 OD unit=50 μg of DNA/ml.

We therefore injected increasing quantities of this product in order to construct a standard curve.

The areas of the peaks corresponding to the retention time of the reference DNA are compared with the standard curve. This enables quantification to be effected.

9. Assay of the Residual Chromosomal DNA

The residual genomic DNA is quantified by means of PCR using primers from within the E. coli galK gene. The sequences of the E. coli galK gene primers are (Debouck et al., Nucleic Acids Res., 1985, 13, 1841–1853):

5' CCG AAT TCT GGG GAC CAA AGC AGT TTC-3' (SEQ ID NO:7) and 5'-CCA AGC TTC ACT GTT CAC GAC GGG TGT-3' (SEQ ID NO:8).

The reaction medium contains, in PCR buffer (Promega France, Charbonnières): 1.5 mM $MgCl_2$; 0.2 mM dXTP (Pharmacia, Orsay); 0.5 μM of primer; 20 U/ml Taq polymerase (Promega). The reaction is carried out in accordance with the sequence: −5 min at 95° C.

30 cycles of 10 sec at 95° C.

30 sec at 60° C.

1 min at 78° C.

10 min at 78° C.

The amplified DNA fragment, which is 124 base pairs in length, is separated by electrophoresis on a 3% agarose gel in the presence of SybrGreen I (Molecular Probes, Eugene, USA) and then quantified by reference to a range of Ultrapur genomic DNA from E. coli strain B (Sigma, ref. D4889).

10. Transfection of Mammalian Cells in vitro

This method is employed for the purpose of assaying the biological activity of the plasmid which has been purified by the process according to the invention. The cells which are used are NIH 3T3 cells which have been seeded, on the day prior to the experiment, in 24-well culture plates at the rate of 50,000 cells/well. The plasmid is diluted in 150 mM NaCl and mixed with a lipofectant. A ratio of positive charges of the lipofectant/negative charges of the DNA equal to 3 is used. The mixture is vortexed, left at ambient temperature for 10 minutes, diluted in culture medium lacking foetal calf serum and then added to the cells at a rate of 1 mg of DNA per well of culture. After two hours at 37° C., 10% v/v of foetal calf serum is added and the cells are incubated at 37° C. for 48 hours in the presence of 5% $CO_2$. The cells are washed twice with PBS and the luciferase activity is measured, in accordance with the described protocol (Promega kit, Prometa Corp. Madison, Wis.), on a Lumat LB9501 luminometer (EG and G Berthold, Evry). The proteins are assayed by the BCA technique (Pierce, Interchim, Asnières).

11. Miscellaneous Techniques

When analysed by electrophoresis on an agarose gel and staining with ethidium bromide, the plasmid which has been obtained appears in the form of a single band of "supercoiled" circular DNA. No trace of high molecular weight (chromosomal) DNA or of RNA is detectable in the purified plasmid.

The protein concentrations in the samples are measured by Micro-BCA (Pierce) in accordance with the manufacturer's instructions.

The endotoxin concentration is evaluated by the LAL (Biosepra) assay in accordance with the manufacturer's instructions.

The standard methods of molecular biology, such as digestions with restriction enzymes, gel electrophoresis, transformation into *E. coli*, precipitation of nucleic acids, etc., are described in the literature (Maniatis et al., T., E. F. Fritsch, and J. Sambrook, 1989. Molecular cloning; a laboratory manual, second edition, Cold Spring Harbor Laboratory, Cold Spring Harbor Laboratory Press, New York,; Ausubel F. M., R. Brent, R. E. Kinston, D. D. Moore, J. A. Smith, J. G. Seidman and K. Struhl, 1987. Current protocols in molecular biology 1987–1988, John Wiley and Sons, New York.). The nucleotide sequences were determined by the chain-termination method in accordance with the above-mentioned protocol (Ausubel et al., 1987).

The restriction enzymes were supplied by New- England Biolabs, Beverly, Mass. (Biolabs).

For the ligations, the DNA fragments are incubated in a 50 mM Tris-HCl, pH7.4, 10 mM $MgCl_2$, 10 mM DTT, 2 mM ATP buffer in the presence of phage T4 DNA ligase (Biolabs).

The oligonucleotides are synthesized using the chemistry of phosphoramidites which are b-protected by a cyanoethyl group (Sinha, N. D., J. Biernat, J. McManus and H. Köster, 1984, Polymer support oligonucleotide synthesis, XVIII: Use of b-cyanoethyl-N,N-dialkylamino-/N-morpholino phosphoramidite of deoxynucleosides for the synthesis of DNA fragments simplifying deprotection and isolation of the final product, Nucl. Acids. Res., 12, 4539–4557; Giles, J. W. 1985, Advances in automated DNA synthesis; Am. Biotechnol., November/December) and employing a Biosearch 8600 automated DNA synthesizer in accordance with the manufacturer's recommendations.

The ligated DNA's, or those to be tested for their transformation efficiency, are used to transform the strain: *E. coli* DH5a [F'/endA1, hsdR17, supE44, thi-1, recA1, gyrA96, relA1, D(lacZYA-argF)U169, deoR, F80dlac(lLacZDM15)] which has been rendered competent.

The minipreparations of plasmid DNA are carried out in accordance with the protocol of Klein et al., 1980.

LB Culture medium is used for growing the *E. coli* strains (Maniatis et al., 1982). The strains are incubated at 37° C. The bacteria are streaked on plates of LB medium supplemented with appropriate antibiotics.

EXAMPLES

Example 1

Purification of a Plasmid DNA on a Ceramic Hydroxyapatite Column 1.1. Preparation of the Clear Lysate
Material:
The following solutions are used in this example:
25 mM Tris, pH 6.8, 50 mM glucose, 10 mM ETDA: solution 1
0.2 M NaOH and 1% SDS: solution 2
3 M potassium acetate, pH 5: solution 3
Method:
200 g of cells are suspended in 2200 ml of solution 1. Solution 2 (also 2200 ml) is then added. Finally 1100 ml of solution 3 are added. The precipitate which has by then been formed is removed by centrifuging at 9000 rpm for 30 min. 5200 ml of supernatant are obtained.

1.2. Diafiltration
Material:
Maximate (Filtron) membrane having a cut-off point of 100 KD and an area of 1860 $cm^2$
Buffer: 100 mM sodium phosphate, pH 6.8
Method:
Before use, the membrane is subjected to chemical decontamination with 0.5 M sodium hydroxide solution for 1 hour. The sodium hydroxide solution is then removed with water for injection.

The supernatant obtained during step 1.1 is concentrated about 10 times and then diafiltered against 4 volumes of water and then against 4 volumes of 100 mM phosphate buffer, pH 6.8. The final volume is 810 ml. The sample then contains 224 mg of plasmid DNA, as determined by HPLC.

1.3. Purification on Ceramic Hydroxyapatite™
Material:
The following buffers are used during this purification:
Buffer A=10 mM phosphate buffer, pH 6.8
Buffer B=150 mM phosphate buffer, pH 6.8
Buffer C=250 mM phosphate buffer, pH 6.8
Buffer D=500 mM phosphate buffer, pH 6.8
0.5 M NaOH
Method:
The column (with a diameter of 113 mm and a height of 17 cm) contains 1700 ml of gel.

Before use, the gel is subjected to chemical decontamination with 0.5M sodium hydroxide solution for 1 hour. The sodium hydroxide solution is then removed by applying buffer D. The column is then equilibrated in buffer A.

610 ml of the previously obtained 810 ml (i.e. 171 mg) are loaded onto the gel. The flow rate is 60 ml/min. The gel is then washed with 6 L of buffer B. After that, the product is eluted by applying buffer C. The eluate has a volume of 1520 ml and contains 147 mg of plasmid DNA (determined by HPLC).

The gel is subsequently regenerated by washing it with sodium hydroxide solution (0.5 M NaOH) following by buffer D. The gel is then ready for a new cycle.

The whole operation is followed by UV spectrometry at 254 nm.

1.4. Purification on DEAE Sepharose
Material:
The following buffers are used in this purification:
Buffer A, 1 M NaCl and 0.5 M NaOH.
Method:
The column (with a diameter of 50 mm and a height of 6 cm) contains 110 ml of gel.

Before use, the gel is subjected to chemical decontamination with 0.5 M sodium hydroxide solution for 1 hour. The sodium hydroxide solution is then removed with a 1 M solution of NaCl. After that, the column is equilibrated in buffer A.

1130 ml of the previously obtained 1520 ml (i.e. 110 mg) are loaded onto the gel at a flow rate of 50 ml/min. Since the DNA is not retained, the effluent is collected (1036 ml) and contains 104 mg of DNA. The products which are retained on the gel are then removed with a 1 M solution of NaCl. After that, the gel is then washed with 0.5 M sodium hydroxide solution followed by 1 M NaCl. The gel is then ready for a new operation.

The whole operation is followed by UV spectrometry at 254 nm.

1.5. Diafiltration

Material:

Ultrasete (Filtron) membrane having a cutoff point of 30 KD and an area of 860 cm$^2$ Buffer: water for injection Method:

Before use, the membrane is subjected to chemical decontamination with 0.5 M sodium hydroxide solution for 1 hour. The sodium hydroxide solution is then removed with the water for injection. 720 ml of the product obtained in the preceding step are concentrated approximately 3 times and then diafiltered twice against 4 volumes of water for injection. The final volume is 210 ml. The sample then contains 62 mg of plasmid DNA, as determined by HPLC.

1.6 Characteristics of the DNA

The above-described process enables the plasmid to be obtained in a virtually pure state. The different components of the final sample were determined and are summarized below.

RNA: not detectable in an agarose gel or by HPLC chromosomal DNA determined by PCR:<0.5% supercoiled DNA determined by HPLC>80% endotoxins (LAL)<50 EU/mg proteins (microBCA)<1 µg/ml biological activity in vitro:

pXL2784 batch 42DNA95: 20×10$^6$ RLU/µg of protein (to be compared with same plasmid purified on a caesium chloride gradient=13×10$^6$ RLU/µg of protein).

1.7 Variant.

The above-described process was duplicated except that, in step 1.1, a filtration through a depth membrane was carried out instead of the centrifugation. This variant of the process makes it possible to obtain a plasmid of pharmaceutical purity whose characteristics are summarized below.

RNA: not detectable in an agarose gel or by HPLC chromosomal DNA determined by PCR:<0.5% supercoiled DNA determined by HPLC>70% endotoxins (LAL)<50 EU/mg proteins (microBCA)<1 mg/ml

Example 2

Purification of the Hydroxyapatite Eluate by Means of Triple Helix Affinity Chromatography 2.1 Preparation of the Affinity Column The column which is used is an NHS (N-hydroxysuccinimide, Pharmacia)-activated HiTrap column of 5 ml which is connected to a peristaltic pump. The specific oligonucleotide which is used possesses a 5' NH$_2$ group. Its sequence is as follows:

5'-GAGGCTTCTTCTTCTTCTTCTTCTT-3' (SEQ ID NO:1).

The following buffers are used in this example:

Coupling buffer: 0.2 M NaHCO$_3$, 0.5 M NaCl, pH 8.3.

Buffer A: 0.5 M ethanolamine, 0.5 M NaCl, pH8.3.

Buffer B: 0.1 M acetate, 0.5 M NaCl, pH 4.

The column is washed with 30 ml of 1 mM HCl, after which the oligonucleotide, diluted in coupling buffer (250 nmol in 5 ml), is loaded onto the column and left at ambient temperature for 30 minutes. The column is washed 3 times, successively, with 30 ml of buffer A and then with 30 ml of buffer B. The oligonucleotide is thereby bound covalently to the column by a CONH bond. The column is stored at 4 C.

2.2. Purification of the Plasmid

The following buffers are used:

Buffer F: 2 M NaCl, 0.2 M acetate, pH 4.5.

Buffer E: 1 M tris-HCl, pH 9, 0.5 mM EDTA.

The column is equilibrated in buffer F and then 9 ml of hydroxyapatite eluate, obtained under the conditions described in Example 1.3., and previously adjusted to 2 M NaCl and pH 4.5, are loaded, in a loop, onto the column at ambient temperature overnight (flow rate 0.5 ml/min). The column is washed with buffer F and elution is then performed with buffer E. The DNA is detected by UV spectrometry at 254 nm.

2.3. Characteristics of the Purified DNA

When analysed by HPLC (method described above), the purified DNA appears in the form of a single peak at a retention time of 24.8 min. There is no detectable trace of RNA. Similarly, after electrophoresis on a 1% agarose gel and staining with ethidium bromide, the purified DNA does not exhibit any detectable trace of RNA.

The DNA was also analysed by anion exchange chromatography on a Waters Gen-Pak Fax column, which separates relaxed DNA from supercoiled DNA. The purified sample contains 97% supercoiled DNA as against 80% supercoiled DNA in the sample which was loaded.

The *E. coli* genomic DNA was quantified by PCR using the technique described in paragraph 3: the DNA which has been purified on the affinity column contains approximately 0.01% genomic DNA.

Example 3

3.1. Purification of the Plasmid

An affinity column is employed which was prepared as described in Example 2 using the oligonucleotide of the sequence:

5'-CTT CTT CTT CTT CTT CTT CTT-3' (SEQ ID NO:2)

The following buffers are used:

Buffer F: 2 M NaCl, 0.2 M sodium acetate, pH 4.5.

Buffer E: 1 M Tris-HCl, pH 9, 0.5 mM EDTA.

The column is equilibrated in buffer F, after which 0.8 mg of plasmid, which has been purified in accordance with the protocol of Example 1.7, and which is diluted in 10 ml of buffer F, is then loaded. The sample is recirculated in a loop through the column at ambient temperature overnight (flow rate 0.5 ml/min). The column is washed with buffer F and elution is then performed using buffer E. The DNA is detected by UV spectrometry at 254 nm.

3.2. Characteristics of the Purified DNA

The DNA which was obtained was analysed by anion exchange chromatography on a Waters Gen-Pak Fax column, which separates relaxed DNA from supercoiled DNA. The purified sample contains 100% supercoiled DNA, as against 72% in the sample which was loaded onto the affinity column.

The *E. coli* genomic DNA was quantified by PCR using the technique described above: the DNA which has been purified on the affinity column contains approximately 0.01% genomic DNA, as against approximately 0.3% in the sample which was loaded onto the affinity column.

Example 4

Changing the Scale of the Triple Helix Affinity Chromatography After Purifying the Hydroxyapatite Eluate (pXL 2784)

4.1. Preparation of the Affinity Column

The column which is employed is a column which contains NHS (N-hydroxysuccinimide, Pharmacia)-activated Sepharose 4 Fast Flow and is coupled to an oligonucleotide of the sequence:

5'-CTT CTT CTT CTT CTT CTT CTT-3' [(CTT)$_7$:SEQ ID NO:2]

in accordance with the method described in Example 2.1.

The column (diameter 26 mm, height: 16 cm) contains 80 ml of gel and is connected to a peristaltic pump.

4.2. Purification of the Plasmid

The following buffers are used:

Buffer F: 2 M NaCl, 0.2 M sodium acetate, pH 4.5.

Buffer E: 1 M Tris-HCl, pH 9, 0.5 mM EDTA.

The column is equilibrated in buffer F, after which 135 ml, i.e. 8 mg, of hydroxyapatite eluate, which has been obtained under the conditions described in Example 1.3. and which has previously been adjusted to 2 M NaCl and pH 4.5, are loaded onto the column (flow rate 1.25 ml/min) by being recirculated four times. The column is washed with buffer F and elution is then performed using buffer E. The DNA is detected by UV spectrometry at 254 nm: 2.2 mg are recovered.

4.3. Characteristics of the Purified DNA

When analysed by HPLC (method described above), the purified DNA appears in the form of a single peak at a retention time of 24.4 min. No trace of RNA is detectable. Similarly, after electrophoresis on a 1% agarose gel and staining with ethidiun bromide, the purified DNA does not exhibit any detectable trace of RNA.

The DNA was also analysed by anion exchange chromatography on a Waters Gen-Pak Fax column, which separates relaxed DNA from supercoiled DNA. The purified sample contains 100% supercoiled DNA, as against 94% supercoiled DNA in the loaded sample.

The *E. coli* genomic DNA was quantified by PCR using the technique described in paragraph 3: the DNA which has been purified on the affinity column contains approximately 0.02% genomic DNA, as against 2% in the loaded sample.

Example 5

Large-scale Purification of a Plasmid DNA on a Ceramic Hydroxyapatite Column 5.1. Preparation of the Clear Lysate The clear lysate is prepared, as described in Example 1.1, from a culture of *E. coli* bacteria which are transformed with plasmid pXL2774. Plasmid pXL2774 is of a reduced size (approximately 4.5 kb) and comprises, in particular:

a cassette for expressing the Luc gene (CMV promoter-luc-poly(A)+)

the sup Phe selection marker the ori g origin of replication from R6K the cer fragment of ColE1

Method:

456 g of cells are suspended in 5000 ml of solution 1. Solution 2 (5500 ml) is then added. Finally, 2500 ml of solution 3 are added. The precipitate which has then formed is removed by centrifuging at 9000 rpm for 30 minutes or by filtering. 12.3 l of supernatant are obtained.

5.2. Diafiltration

Material:

Maximate (Filtron) membrane having a cut-off point of 100 kD and an area of 1860 cm$^2$ Buffer: 100 mM sodium phosphate, pH 6.8

Method:

The sample is diafiltered in accordance with the method described in Example 1.2.

The final volume is 945 ml. The sample then contains 253 mg of plasmid DNA as determined by HPLC.

5.3. Purification on Ceramic Hydroxyapatite™

Material:

The following buffers are used in this purification:

Buffer A=100 mM phosphate buffer, pH 6.8

Buffer B=150 mM phosphate buffer, pH 6.8

Buffer C=250 mM phosphate buffer, pH 6.8

Buffer D=500 mM phosphate buffer, pH 6.8

0.5 M NaOH

Method:

The column (which has a diameter of 100 mm and a height of 23 cm) contains 1700 ml of gel.

Before use, the gel is subjected to chemical decontamination with 0.5 M sodium hydroxide solution for 1 hour. The sodium hydroxide solution is then removed by applying buffer D. After that, the column is equilibrated in buffer A.

475 ml of the previously obtained 945 ml (i.e. 128 mg) are loaded onto the gel. The flow rate is 65 ml/min. The gel is then washed with 6 l of buffer B. The product is subsequently eluted by applying buffer C. The eluate has a volume of 1760 ml and contains 100 mg of plasmid DNA (determined by HPLC).

The gel is subsequently regenerated by washing it with sodium hydroxide solution (0.5 M NaOH) followed by buffer D. The gel is then ready for a new cycle.

The whole operation is followed by UV spectrometry at 254 nm.

5.4. Diafiltration

The diafiltration was carried out in accordance with the protocol described in Example 1.5.

5.5 Characteristics of the DNA

The above-described process enables the plasmid to be obtained in a virtually pure state. The different components of the final sample were determined and are summarized below.

RNA: not detectable in an agarose gel chromosomal DNA determined by PCR: 0.6% supercoiled DNA determined by HPLC: 87% endotoxins (LAL)<50 EU/mg proteins (microBCA)<1 mg/ml

What is claimed is:

1. In a process for purifying double-stranded DNA comprising lysing cells followed by one or more chromatographic separation steps, the improvement comprising separating the DNA from other biological material in admixture therewith using ceramic hydroxyapatite column chromatography.

2. A process according to claim 1 for purifying double-stranded DNA, comprising using two chromatographic steps, of which one is ceramic hydroxyapatite column chromatography.

3. The process according to claim 2, further comprising using affinity chromatography or ion exchange chromatography.

4. The process according to claim 3, wherein the affinity chromatography involves triple helix formation between the DNA and an immobilized oligonucleotide.

5. The process according to claim 3, wherein the ion exchange chromatography is anion exchange chromatography.

6. The process according to claim 1, further comprising a step of diafiltration.

7. The process according to claim 2, further comprising a step of diafiltration.

8. The process according to claim 3, further comprising a step of diafiltration.

9. The process according to claim 4, further comprising a step of diafiltration.

10. The process according to claim 5, further comprising a step of diafiltration.

11. A process for purifying double-stranded DNA, comprising chemical lysing of cells, diafiltration;

using ceramic hydroxyapatite column chromatography, and using affinity chromatography involving triple helix formation between the DNA and an immobilized oligonucleotide.

12. The process according to claim 1, wherein the double-stranded DNA is a plasmid.

13. The process according to claim 2, wherein the double-stranded DNA is a plasmid.

14. The process according to claim 3, wherein the double-stranded DNA is a plasmid.

15. The process according to claim 4, wherein the double-stranded DNA is a plasmid.

16. The process according to claim 5, wherein the double-stranded DNA is a plasmid.

17. The process according to claim 6, wherein the double-stranded DNA is a plasmid.

18. The process according to claim 7, wherein the double-stranded DNA is a plasmid.

19. The process according to claim 8, wherein the double-stranded DNA is a plasmid.

20. The process according to claim 9, wherein the double-stranded DNA is a plasmid.

21. The process according to claim 10, wherein the double-stranded DNA is a plasmid.

22. The process according to claim 11, wherein the double-stranded DNA is a plasmid.

* * * * *